(12) United States Patent
Ludwig et al.

(10) Patent No.: US 6,605,070 B2
(45) Date of Patent: Aug. 12, 2003

(54) ABSORBENT ARTICLE HAVING SELECTIVELY CHANGEABLE SIZE ADJUSTMENT

(75) Inventors: Susan J. Ludwig, Cincinnati, OH (US); Gary D. Lavon, Middletown, OH (US)

(73) Assignee: The Procter & Gamble Company, Cincinnati, OH (US)

(*) Notice: Subject to any disclaimer, the term of this patent is extended or adjusted under 35 U.S.C. 154(b) by 22 days.

(21) Appl. No.: 09/896,260

(22) Filed: Jun. 29, 2001

(65) Prior Publication Data

US 2003/0009143 A1 Jan. 9, 2003

(51) Int. Cl.⁷ ................................................ A61F 13/20
(52) U.S. Cl. ......................... 604/385.22; 604/385.23; 604/385.24; 604/385.29
(58) Field of Search .................. 604/385.01, 385.04, 604/385.21–385.24, 385.29–385.3

(56) References Cited

U.S. PATENT DOCUMENTS

| | | | |
|---|---|---|---|
| 4,107,364 A | | 8/1978 | Sisson |
| 4,834,741 A | | 5/1989 | Sabee |
| 5,167,897 A | | 12/1992 | Weber et al. |
| 5,518,801 A | | 5/1996 | Chappell et al. |
| 5,650,214 A | | 7/1997 | Anderson et al. |
| 5,688,259 A | * | 11/1997 | Osborn et al. ......... 604/385.01 |
| 5,702,382 A | | 12/1997 | Osborn, III et al. |
| 5,807,368 A | * | 9/1998 | Helmer ..................... 604/373 |
| 5,904,673 A | | 5/1999 | Roe et al. |
| 5,938,652 A | * | 8/1999 | Sauer ..................... 604/385.29 |
| 6,264,639 B1 | | 7/2001 | Sauer |
| 6,264,641 B1 | * | 7/2001 | Van Gompel et al. .. 604/385.22 |
| 6,264,642 B1 | | 7/2001 | Kuen et al. |
| 6,414,217 B1 | * | 7/2002 | Uitenbroek et al. ......... 604/378 |

FOREIGN PATENT DOCUMENTS

| | | | | |
|---|---|---|---|---|
| WO | WO 00/30584 A1 | 6/2000 | | |
| WO | WO 01/82849 A1 | 11/2001 | | |
| WO | WO 01/82851 A1 | * 11/2001 | ........... | A61F/13/15 |
| WO | WO 01/82852 A1 | 11/2001 | | |
| WO | WO 02/069870 A2 | 9/2002 | | |

* cited by examiner

Primary Examiner—Gregory L. Huson
Assistant Examiner—Amanda Flynn
(74) Attorney, Agent, or Firm—Jay A. Krebs; Ken K. Patel

(57) ABSTRACT

An absorbent article includes a liquid impervious backsheet joined to a liquid permeable topsheet with an absorbent core disposed therebetween. The joined topsheet and backsheet includes an extensible portion that is non-elastically, laterally extensible having a percent elongation of at least about 125%. A pair of elastomeric side panels is joined to a portion of the joined topsheet and backsheet near the extensible portion. Each of the side panels is elastically laterally extensible such that the force required to elongate the side panels a select percent elongation is less than the force required to elongate the extensible portion of the joined topsheet and backsheet an equivalent select percent elongation.

20 Claims, 3 Drawing Sheets

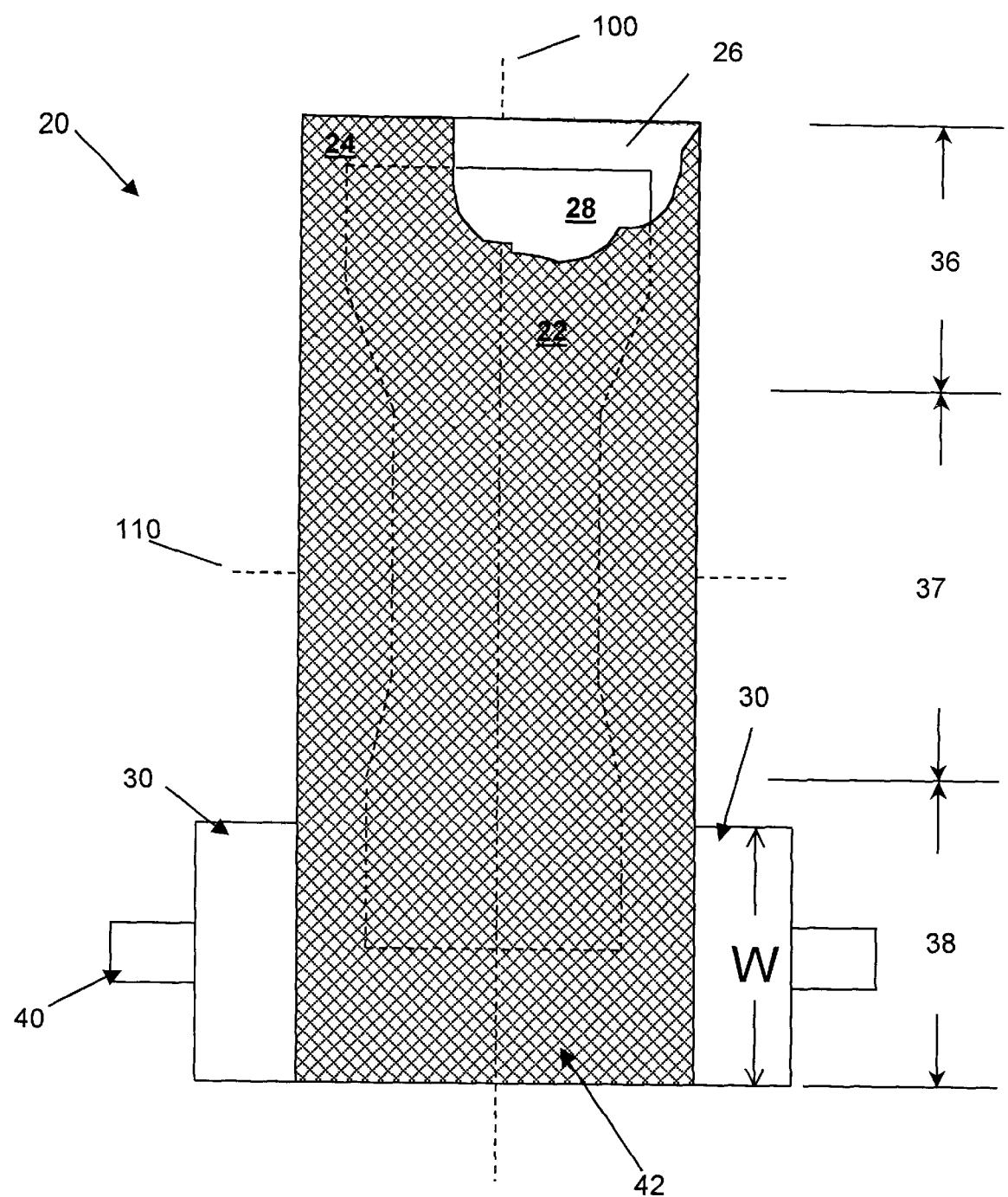
Figure: 1

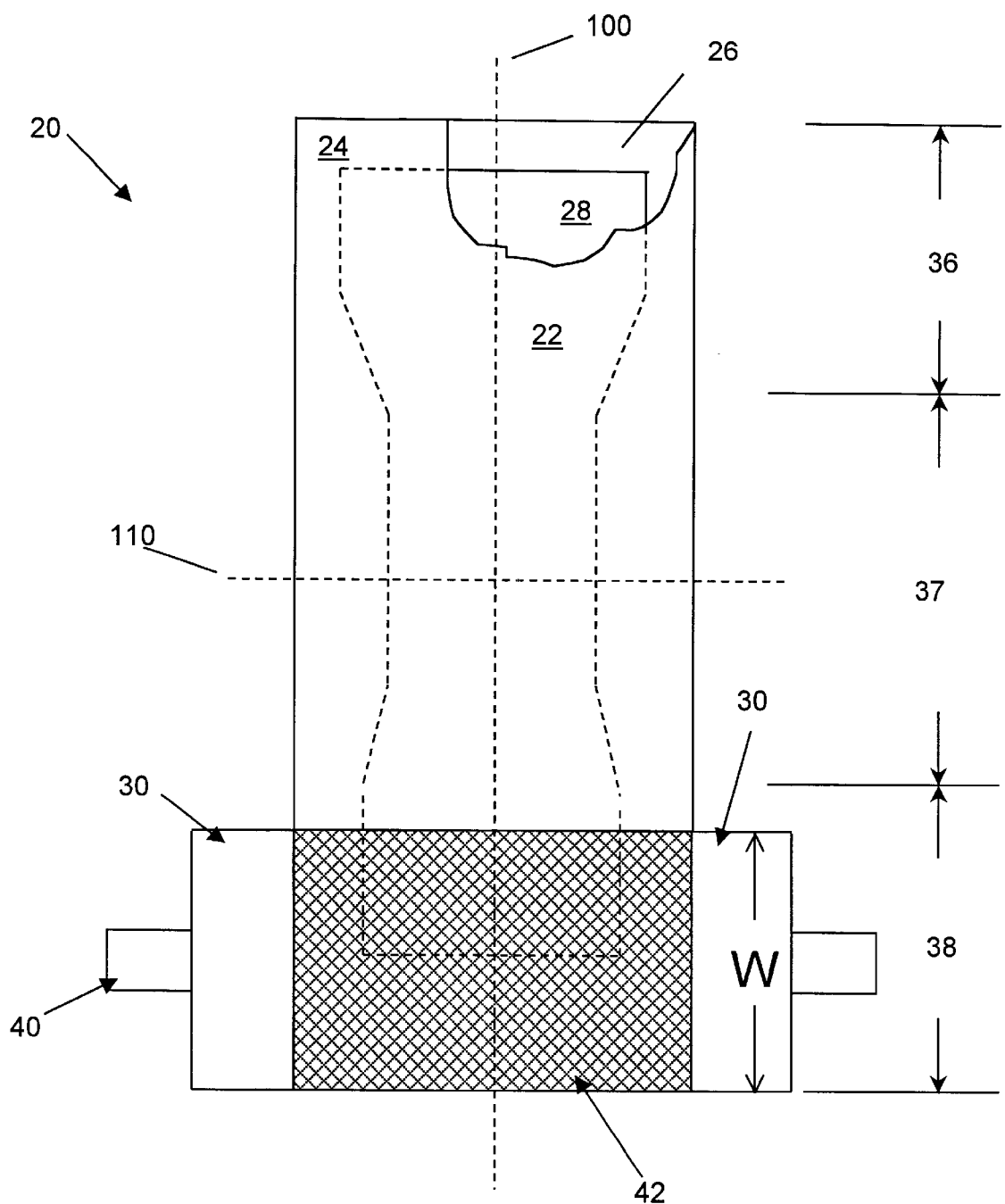
Figure: 2

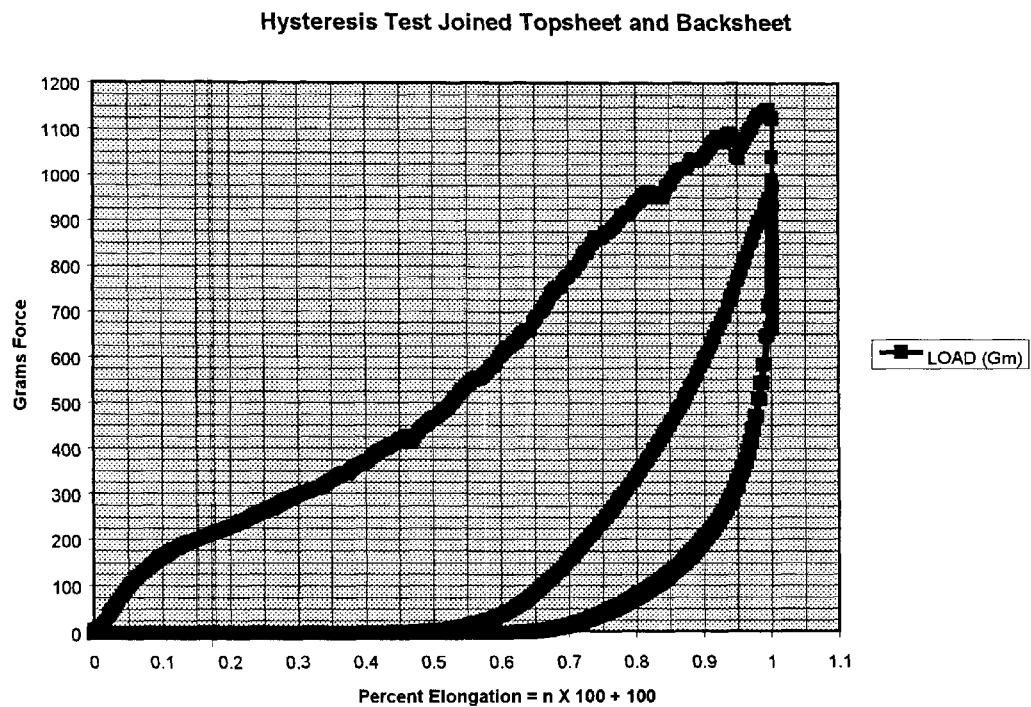
Figure: 3
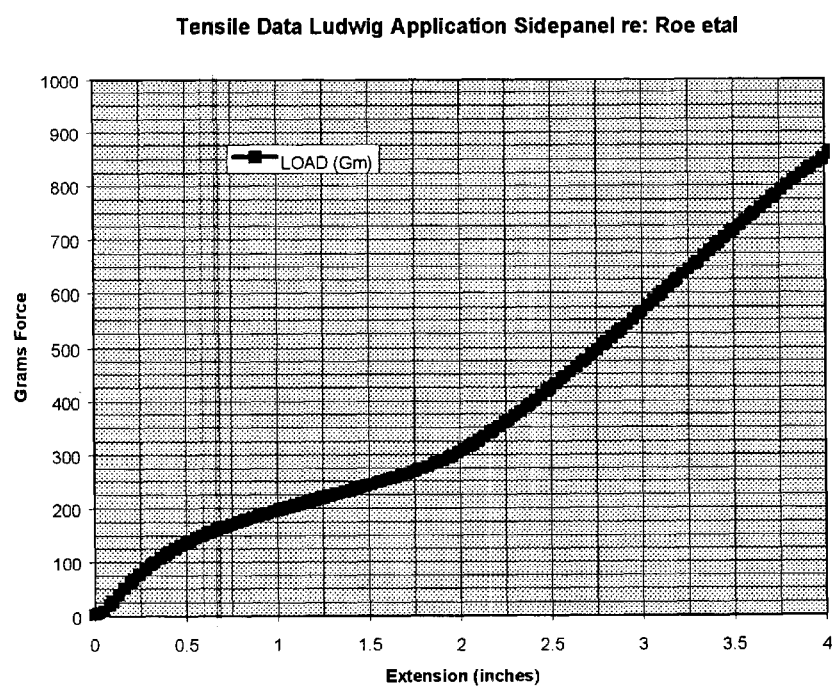
Figure: 4

ABSORBENT ARTICLE HAVING SELECTIVELY CHANGEABLE SIZE ADJUSTMENT

FIELD OF THE INVENTION

The present invention relates to disposable absorbent articles, such as disposable diapers.

BACKGROUND OF THE INVENTION

Infants and other incontinent individuals wear absorbent articles such as diapers and incontinent briefs to receive and contain discharged urine and other body exudates. Such absorbent articles function both to contain the discharged materials and to isolate those materials from the body of the wearer and from the wearer's garments and bed clothing. Disposable absorbent articles having many different basic designs are known in the art. For example, U.S. Reissue Pat. No. Re. 26,152, entitled "Disposable Diaper," which issued on Jan. 31, 1967, to Duncan et al., describes a basic disposable diaper structure that has achieved wide acceptance and considerable commercial success.

Fit, comfort, and skin health of the wearer continue to be sought-after attributes in diaper design and manufacture. Despite recent improvements in comfort and fit due to the utilization of breathable materials, as well as, elastic materials, absorbent articles continue to be sold and marketed in many different sizes due to the varying body dimensions and anatomical characteristics of the intended wearers of such absorbent articles. Currently marketed diaper sizes are primarily distinguished by weight, such that a consumer can select a certain diaper based on the weight of the baby or child for which the article is intended. However, due to various body differences among babies, and the nature of limited choices in discrete diaper sizes, often a given diaper size does not fit as well as desired.

The variations in anatomical shape, even for babies of similar weight, can be quite extreme often leading to improper fit of the absorbent article, even when the appropriate size product, based on weight, is used. These variations in baby shape and size are especially pronounced for smaller babies, particularly premature or newborn babies weighing between 400 and 2300 grams. These newborn babies, who in many cases can literally fit in the palm of an adult hand, have special diapering needs in general. These needs include adequate urine absorption and isolation in a narrow crotch product design, heightened importance of skin health, proper, customizable, and comfortable fit, as well as ease of use to minimize handling by doctors and nurses.

Premature babies can also change in weight rather rapidly such that in a matter of days a given premature baby can outgrow a once properly fitting diaper. Current commercially available products for premature babies come in at least three sizes, none of which provide a proper comfortable fit. That is, they can be too big for babies on the smaller end of the size range, or too small for larger babies. To adequately fit the various sizes and shapes of these babies and accommodate rapid growth, multiple sizes of products would be required. This, however, would place a significant burden on manufacturers to make and distribute (and hospitals to purchase and inventory) the various discrete sizes of product.

Accordingly, there is a need for a disposable diaper that can be configured or adjusted by the user to properly fit the wearer to better accommodate rapid growth and anatomical shape variations while adequately absorbing and isolating body exudates such as urine and feces. Additionally, there is a need for a disposable diaper that can properly and comfortably fit a wide range of sizes.

SUMMARY OF THE INVENTION

In accordance with the present invention, there is provided an absorbent article that is worn about the waist and lower torso of the wearer. The article includes a substantially liquid impervious backsheet having an outer, garment-facing surface and an inner, body-facing surface. An absorbent core is provided adjacent the body-facing surface of the backsheet. A flexible, liquid pervious topsheet overlies the absorbent core and is joined to the backsheet. The absorbent article includes two extensible side panels, which extend laterally away from the longitudinal edges of the joined topsheet and backsheet, preferably in the rear of the product, and an extensible portion of the joined topsheet and backsheet combination that is also laterally extensible. The side panels are preferably elastically extensible while the extensible portion of the joined topsheet and backsheet is non-elastically extensible such that it is capable of being elongated to a permanent set or permanent deformation. The force required to elongate the side panels is lower than the force required to elongate the extensible portion of the topsheet and backsheet such that the side panels can undergo a substantial elastic extension before the extensible portion of the joined topsheet and backsheet undergoes permanent deformation.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 1 is a plan view of a disposable diaper with the extensible portion of the joined topsheet and backsheet including the first waist region, the second waist region and the crotch region.

FIG. 2 is a plan view of a disposable diaper with the extensible portion of the joined topsheet and backsheet disposed in the second waist region.

FIG. 3 is a graph of Grams Force vs. Percent Elongation (×100) for the extensible portion of the joined topsheet and backsheet shown in FIG. 1 when subjected to 100% elongation and examined for hysteresis response.

FIG. 4 is a graph of Grams Force vs. Extension (inches) for the side panel illustrated in FIG. 1.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included drawings.

Definitions

As used herein, the term "absorbent article" refers to devices that absorb and contain body exudates, and more specifically, refers to devices that are placed against or in proximity to the body of the wearer to absorb and contain the various exudates discharged from the body.

As used herein, the term "disposable" refers to absorbent articles that are not intended to be laundered or otherwise restored or reused as an absorbent article (i.e., they are intended to be discarded after a single use and, preferably, to be recycled, composted or otherwise disposed of in an environmentally compatible manner).

As used herein, the term "diaper" refers to an absorbent article generally worn by infants and incontinent persons about the lower torso.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. A "unitary" absorbent article refers to absorbent articles which are formed of separate parts united together to form a coordinated entity so that they do not require separate manipulative parts like a separate holder and liner.

As used herein, the term "extensible" is used to refer to materials that can be extended in a direction corresponding to a biasing force.

As used herein the term "percent elongation" refers to the percentage increase in a material's length due to a biasing force. For the present invention, percent elongation is measured such that a material having a relaxed, unbiased length of one (1) inch (2.54 cm) that is stretched to a length of one and one half (1.5) inches (3.81 cm), has a percent elongation of 150%.

As used herein, the term "recover" refers to a contraction of a stretched material upon termination of a biasing force following stretching of the material by application of the biasing force. For example, if a material having a relaxed, unbiased length of one (1) inch (2.54 cm) were elongated to 150 percent by stretching to a length of one and one half (1.5) inches (3.81 cm) the material would have a stretched length that is 150 percent of its relaxed length. If this exemplary stretched material contracted, that is, recovered, to a length of one and one tenth (1.1) inches (2.79 cm) after release of the biasing and stretching force, the material would have recovered 80 percent (0.4 inch, 1.02 cm) of its elongation.

As used herein, the terms "elastic" or "elastomeric" refer to any material which upon application of a biasing force, is stretchable to a stretched, biased length which is at least about 150 percent, or one and a half times, its relaxed, non stretched length, and which will recover at least 60 percent of its elongation upon release of the stretching, biasing force. Preferably these elastically extensible materials will recover at least 75% of its elongation upon release of the stretching, biasing force.

As used herein, the terms "non-elastic" and "non-elastomeric" refer to any material that is not elastic or elastomeric, respectively, as defined above.

As used herein, the term "non-elastically extensible" refers to materials that can be extended in a direction corresponding to a biasing force but which have little or no significant recovery associated with such extension. For example, a material which upon application of a biasing force, is extended to a biased length which is at least about 150 percent, or one and a half times, its relaxed, non extended length, and which recovers less than 60 percent of its elongation upon release of the biasing force would be considered non elastically extensible as used herein. A preferred non elastically extensible material utilized in the present invention is one, which, upon application of a biasing force can be extended to a biased length which is at least about 150 percent its relaxed, non extended length, and recovers less than 50 percent, preferably less than 30 percent, of its elongation upon release of the biasing force.

As used herein, the term "laterally" in reference to extensibility refers to extension in a direction generally orthogonal to the longitudinal axis 100, and generally parallel to the transverse axis 110.

The present invention provides a disposable absorbent design having selective size adjustment. The absorbent article comprises a liquid impervious backsheet, a liquid permeable topsheet joined to the backsheet with an absorbent core disposed therebetween. The joined topsheet and backsheet includes an extensible portion, which is non-elastically extensible, and two elastically extensible side panels disposed along longitudinal edges of the joined topsheet and backsheet near the extensible portion. The force required to elongate the side panels is lower than the force required to elongate the extensible portion of the joined topsheet and backsheet. The initial fit of the product to a wearer is adjusted by the extension of the side panels. Once the side panels have been extended to a point of becoming inadequate to provide proper fit, applying a sufficient lateral force may permanently set or deform the extensible portion of the joined topsheet and backsheet in an extended condition to enlarge the article. Once enlarged, the absorbent article can be applied to the wearer, utilizing the stretch in the side panels to provide the closure and proper fit to the wearer. The design is equally applicable to disposable absorbent articles including disposable diapers, training pants, incontinence briefs, incontinence undergarments, absorbent inserts, diaper holders and liners, feminine hygiene garments, and the like. A preferred embodiment of an absorbent article of the present invention is the unitary disposable absorbent article, diaper 20, shown in FIG. 1.

FIG. 1 is a plan view of the diaper 20 in its flat out, uncontracted state (i.e., without elastic induced contraction) with portions of the structure being cut away to more clearly show the underlying structure of the diaper 20 and with the portion of the diaper 20 which contacts the wearer facing the viewer. The diaper 20 includes a longitudinal axis 100 and a transverse axis 110. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions, 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The chassis 22 of the diaper 20 comprises the main body of the diaper 20. The chassis 22 comprises an outer covering including a liquid pervious topsheet 24 and/or a liquid impervious backsheet 26 and at least a portion of an absorbent core 28 encased between the topsheet 24 and the backsheet 26. For unitary absorbent articles, the chassis 22 comprises the main structure of the diaper with other features added to form the composite diaper structure. While the topsheet 24, the backsheet 26, and the absorbent core 26 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 24 may be fully or partially elasticized or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

Topsheet 24 is preferably extensible, comprising a single web of nonwoven material, but can also be a laminate or composite material. The topsheet 24 is preferably non-elastically extensible, which permits it to extend in a direction, with little or no recovery when the forces to extend are removed. Extensible topsheet 24 may be made extensible by methods known in the art, including neck stretching to form a reversibly necked material as disclosed in U.S. Pat. No. 4,965,122 issued to Mormon on Oct. 23, 1990, incorporated herein by reference. Other method of forming an extensible topsheet 24 include a mechanical operations, such as pleating, corrugating, or ring rolling the topsheet material to provide folds in the topsheet that are able to open when the topsheet is extended in a direction orthogonal to the pleats or folds. Suitable processes for ring rolling or pre-corrugating, including topsheets made thereby, are described in U.S. Pat. No. 4,107,364 issued to Sisson on Aug. 15, 1978; U.S. Pat. No. 4,834,741 issued to Sabee on May 30, 1989; U.S. Pat. No. 5,167,897 issued to Weber et al. on Dec. 1, 1992, and U.S. Pat. No. 5,702,382 issued to Osborn, III et al. on Dec. 30, 1997, each of which are hereby incorporated herein by reference.

Topsheet 24 may be apertured. Suitable methods for forming apertured topsheets, and suitable apertured topsheets are disclosed in U.S. Pat. No. 5,628,097 issued to Benson et al. on May 13, 1997; U.S. Pat. No. 5,658,639 issued to Curro et al. on Aug. 19, 1997; and U.S. Pat. No. 5,916,661 issued to Benson et al. on Jun. 29, 1999, each of which are incorporated herein by reference. Other methods of forming apertured nonwoven webs may be utilized, such as those taught in U.S. Pat. No. 5,714,107 issued to Levy et al. on Feb. 3, 1998, and hydroforming processes taught by U.S. Pat. No. 4,840,829 issued to Suzuki et al. on Jun. 20, 1989.

Topsheet 24 may be a formed film rendered extensible by the methods disclosed below. Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 24 can be made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The backsheet 26 is generally that portion of the diaper 20 positioned adjacent the garment-facing surface of the absorbent core 28. Backsheet 26 prevents the exudates absorbed and contained therein from soiling articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The topsheet 24, backsheet 26, and/or the absorbent core 28 may be joined to one another or any other element of the diaper 20 by any attachment means known in the art, as long as the non-elastic extension characteristics of the joined topsheet and backsheet are enabled and/or maintained. For example, in a preferred embodiment, the backsheet 26 and/or the topsheet 24 can be adhesively joined to each other about portions of their respective perimeters, and to relatively non-extensible elements, such as the absorbent core 28, by a relatively narrow bead of adhesive 2 to 4 mm wide applied on or near the longitudinal axis 100 of diaper 20. As such, the bonding of components has minimal impact on the lateral extension properties of the diaper components.

The topsheet 24 is preferably positioned adjacent the body-facing surface of the absorbent core 28 and may be joined thereto and/or to the backsheet 26 by any attachment means known in the art providing lateral extension properties are preserved. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

Other joining means may include a uniform continuous layer of adhesive, a patterned layer of adhesive, or an array of separate lines, spirals, or spots of adhesive providing lateral extension properties are preserved. One preferred configuration of the topsheet, backsheet and absorbent core comprises a single relatively narrow longitudinal line of adhesive disposed generally centrally on both sides of the absorbent core 28 (including other components associated with the core, such as a wrap of tissue, nonwoven, and the like), such that the backsheet 26 is tacked down at locations on the absorbent core 28 generally in line with the longitudinal axis 100. In this manner, the backsheet 26, or portions of the backsheet 26 can be extended laterally as disclosed herein, being substantially decoupled from the absorbent core. To the extent that lateral extension of the backsheet 26 is preserved, other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The diaper 20 also comprises side panels 30, which can be seamed or welded to topsheet 24 and/or backsheet 26. The side panels 30 are elastomeric to provide a more comfortable and body-conforming fit by initially conformably fitting the diaper 20 to the wearer and sustaining this fit throughout the time of wear. Since the elasticized side panels 30 allow the sides of the diaper 20 to expand and contract, the fit is sustained even after diaper 20 has been loaded with exudates. The side panels 30 may also provide more effective application of the diaper 20 because even if the caregiver pulls one elasticized side panel 30 farther than the other during application, the diaper 20 can "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations provided they have the requisite elastomeric characteristics. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

A diaper of the present invention can be designed such that as a caregiver puts a diaper on a wearer "as is" (i.e., without manually initiating lateral extension of the joined topsheet and backsheet), all the initial extension in the waist portions comes from the elastically extensible side panels. Thus, for side panels having significant lateral elastomeric extensibility, the diaper 20 of the present invention can be used on an appropriate-sized wearer "as is" without additional user configuration. However, in order to accommodate larger wearers, the joined topsheet and backsheet, or at least a portion thereof, can be non-elastically extended, as defined herein, to permit the diaper 20 to be fitted to a wide range of users.

For a diaper of the present invention, at least a portion of the joined backsheet 26 and topsheet 24 is preferably laterally extensible; that is, extensible in a direction generally orthogonal to the longitudinal axis 100. However, to fit the lower range of sizes, for example, the smallest babies in a range, it is preferred that the backsheet and topsheet not extend significantly under normal tensioning forces induced during fitting. Thus, the joined topsheet/backsheet combination of the present invention preferably has a minimal biasing force (e.g., tensioning force) required to initiate non-elastic extension of the joined topsheet 24 and backsheet 26. Once extension has been initiated, the extensible portion 42 of the joined topsheet 24 and backsheet 26 can be extended to a useful degree without failure, significant distortion, or other significant degradation to the topsheet 24, backsheet 26, or other diaper components. Preferably, the extensible portion 42 of the joined topsheet 24 and backsheet 26 can be laterally elongated from about 110% to about 200% without a significant decrease in material properties (e.g., liquid impermeability, necking, stretch thinning, and the like).

The extensible portion 42 of the joined topsheet and backsheet may include the first waist region 36, the second waist region 38, and the crotch region 37, as shown in FIG. 1. Alternatively, the extensible portion 42 of the joined topsheet and backsheet may be limited to the first waist region 36 or the second waist region 38. In a preferred embodiment, the extensible portion 42 of the joined topsheet and backsheet is disposed in the second waist region 38 of the diaper 20, as shown in FIG. 2. Preferably, the extensible portion 42 of the joined topsheet 24 and backsheet 26 disposed in the second waist region 38 has a width relative to the longitudinal axis 100 and a length relative to the transverse axis 110 wherein the width is in alignment with the side panels 30. Alternatively, the extensible portion 42 is equal in width to the width W of the side panels 30 and in alignment therewith as shown in FIG. 2.

By designing the joined topsheet 24 and backsheet 26 to have portions that are extensible, under a minimum, predetermined force, the diaper 20 can be "user configurable", adjustable, to permit custom fitting of varying shapes and sizes of wearers, such as babies. For example, for embodiments including a non-elastically extensible portion in the second waist region 38 of the joined topsheet and backsheet, a caregiver can grasp the sides of the second waist region 38 and pull outwardly in a direction generally orthogonal to the longitudinal axis 100 to laterally extend the rearward portion of the diaper forming a somewhat "fanned out" configuration, which increases the size. The extensible portion of the topsheet and backsheet, is substantially non-elastically extensible having a percent elongation of at least about 125% of its initial lateral dimension, preferably at least about 150% of its initial lateral dimension and more preferably, at least about 200% of its initial lateral dimension. Preferably, the extensible portion can be elongated at least about 150%, with little or no recovery.

In a diaper of the present invention, which provides for user configurable size adjustments, it is preferred, that the forces to laterally extend the elastomeric side panels to a useful degree be less than the forces necessary to initiate significant elongation of the joined topsheet and backsheet. In preferred embodiments, the force required to extend the side panel to 150 percent elongation is less than the force required to extend the extensible portion 42 of the joined topsheet and backsheet to 125 percent elongation. It is also preferred that the force required to extend the side panel about 200 percent elongation be less than the force required to extend the extensible portion of the topsheet and backsheet about 150 percent elongation.

For the diaper 20 of the present invention, the biasing forces required to extend the side panel 30 and the biasing forces necessary to extend the joined topsheet 24 and backsheet 26 may be reported as a force per unit length. The forces required to extend the side panel 30 about 125% is preferably less than about 80 g/cm. The forces required to extend the side panel 30 about 150% is preferably less than about 180 g/cm. More preferably, the force required to extend the side panel 30 about 150% ranges from about 60 g/cm to about 120 g/cm.

Similarly, for a diaper 20 of the present invention, the force required to elongate the joined topsheet and backsheet to a percent elongation of about 125% is typically greater than about 80 g/cm. The force required to elongate the joined topsheet 24 and backsheet 26 to a percent elongation of about 150% is at least about 100 g/cm. In preferred embodiments, the force required to elongate the joined topsheet and backsheet a percent elongation of about 125% is between about 60 g/cm and about 160 g/cm, while the force required to extend the joined topsheet and backsheet to a percent elongation of about 150% is preferably between about 100 g/cm and about 225 g/cm.

Without being bound by theory, it is believed that the resistance to extension of the joined topsheet 24 and backsheet 26 can be provided by the backsheet 26, topsheet 24 or a third material that is joined to either the topsheet or backsheet of the joined topsheet and backsheet combination. In an embodiment where the topsheet provides the resistance to extension, the topsheet may be non elastically extensible such that the force required to elongate the topsheet about 125% is greater than the force required to elongate the backsheet about 125% and/or the force required to elongate the topsheet about 150% is greater than the force required to elongate the backsheet about 150%. Similarly, in an embodiment where the backsheet provides the resistance to extension, the backsheet may be non elastically extensible such that the force required to elongate the backsheet about 125% is greater than the force required to elongate the topsheet about 125% and/or the force required to elongate the backsheet about 150% is greater than the force required to elongate the topsheet about 150%.

In an embodiment including a third material joined to the topsheet or the backsheet providing resistance to extension in the extensible portion 42 of the joined topsheet and backsheet, the additional material may be non elastically extensible such that the force required to elongate the third material about 125% is greater than the force required to elongate the topsheet or the backsheet about 125% and/or the force required to elongate the third material about 150% is greater than the force required to elongate the topsheet or the backsheet about 150%. For this embodiment, the third material may be pleated or folded whereby, as the extensible portion is laterally extended, the pleats or folds separate allowing the third material to expand.

Preferably, the force to extend the joined topsheet 24 and backsheet 26, as well as other stress/strain characteristics, are influenced by the configuration of the backsheet and the materials from which the backsheet 26 and/or topsheet 24 are made. In general, it is preferred that there be sufficient resistance in the joined topsheet and backsheet composite to prevent it from extending when subjected to a very small biasing force. Likewise, it is preferred that the joined topsheet and backsheet provide sufficient extension under moderate to high extension forces, to allow for resizing of the product.

Backsheet 26 may be rendered extensible by methods known in the art, including mechanical operations, such as pleating, corrugating, or ring rolling to provide folds that are able to open when the backsheet is extended in a direction generally orthogonal to the pleats or folds. Additionally, the pleats or folds may incorporate a joining means, such as adhesives or other bonding means that are separable thereby allowing the pleats or folds to open providing the necessary extensibility of the extensible portion of the backsheet. Suitable processes for ring rolling or pre-corrugating, including extensible webs made thereby, are described in U.S. Pat. No. 4,107,364 issued to Sisson on Aug. 15, 1978; U.S. Pat. No. 4,834,741 issued to Sabee on May 30, 1989; U.S. Pat. No. 5,167,897 issued to Weber et al. on Dec. 1, 1992, and U.S. Pat. No. 5,702,382 issued to Osborn, III et al. on Dec. 30, 1997, each of which are hereby incorporated herein by reference.

In a preferred embodiment, either the topsheet 24 or the backsheet 26 (more preferably the backsheet 26) includes a thermoplastic film, such as a polyethylene film, made extensible by forming a strainable network having at least two contiguous, distinct, and dissimilar regions. Films thus formed have in the past been termed structural elastic-like films ("SELF"). A structural elastic-like film or web is an extensible material that can exhibit an elastic-like behavior in the direction of elongation without the use of added elastic materials. SELF webs suitable for the present invention, and methods of forming SELF webs suitable for use as backsheets 26, are more completely described in U.S. Pat. No. 5,518,801 entitled Web Materials Exhibiting Elastic-Like Behavior, issued to Chappell, et, al. on May 21, 1996; U.S. Pat. No. 5,650,214 entitled Web Materials Exhibiting Elastic-Like Behavior and Soft, Cloth-like Texture, issued to Anderson et al. on Jul. 22, 1997; and U.S. Pat. No. 5,904,673 entitled Absorbent Article with Structural Elastic-like Film Web Waist Belt, issued to Roe et al. on May 18, 1999, all of which are hereby incorporated herein by reference. For film/nonwoven laminate backsheet, the processes described in the above-mentioned patents can be performed on the laminate material, or on the separate components prior to lamination, or both. In alternate embodiments, the backsheet 26 may comprise elastomeric films, foams, strands, or combinations of these or other suitable materials with nonwovens or synthetic films.

SELF webs can also be made which exhibit minimal elastic behavior. In particular, webs comprising a laminate of films and nonwovens can be made which exhibit little elastic behavior beyond very low levels of strain. The SELF backsheet of a preferred embodiment of the invention does not exhibit an elastic-like behavior to a significant degree when extended beyond about 105%–110% strain. That is, beyond about 105%–110% percent elongation in a direction generally orthogonal to the longitudinal axis 100 and generally parallel to lateral axis 110, the backsheet 26 exhibits little or no elasticity and can be described as non-elastically extensible.

The SELF backsheet can be a laminate of a film and a nonwoven material, and is characterized by a strainable network having at least two contiguous, distinct, and dissimilar regions. Preferably, one of the regions (i.e., a first region) is configured so that it will exhibit initial resistive forces in response to an applied axial elongation in a direction parallel to a predetermined axis before a substantial portion of the other region (i.e., a second region) develops significant resistive forces to the applied elongation. The second region has a surface-path length that is greater than that of the first region as measured substantially parallel to a predetermined axis while the material is in a non-tensioned condition. The second region exhibits one or more deformations that extend beyond the plane of the first region.

The SELF backsheet exhibits at least two significantly different stages of controlled resistive force to elongation along at least one predetermined axis when subjected to an applied elongation in a direction parallel to the predetermined axis. The SELF backsheet exhibits first resistive forces to the applied elongation until the elongation of the web is sufficient to cause a substantial portion of the second region to enter the plane of applied elongation, whereupon the SELF-backsheet exhibits second resistive forces to further elongation. Thereafter, the resistive forces to elongation provided by the second region are higher than the initial resistive forces to elongation provided by the first region.

The difference in resistive forces of the first and second portions of the SELF web, permits the ability to "program in" or control the resistive forces, which is important to the design and operation of a preferred embodiment of the present invention. By selectively predetermining the relative size and configuration of first portions to second portions, the first portion can be designed to exhibit a predetermined first resistive force in response to an applied axial elongation in a direction parallel to a predetermined axis before a substantial portion of the a second portion develops significant resistive forces (i.e., second resistive forces). Therefore, the backsheet remains in a non-extended state until such first resistive force is applied.

The amount of first portion in the SELF-web is the primary factor in determining the minimal force necessary to extend backsheet 26, therefore, the presence of sufficient first portion keeps the SELF-web from extending until a minimum biasing force equal to the first resistive force is applied. The amount and configuration of the second portion of the SELF-web, is the primary factor in determining the extent of stretch available under a biasing force equal to the first resistive force, and the greater the surface-path length of the second portion, the greater the amount of extension under the first resistive force.

In an alternate embodiment, the SELF backsheet may be configured to vary the extensibility of the joined topsheet and backsheet transversely across the width of the chassis 22. For instance, where the core is attached to the backsheet along the longitudinal axis, the extensibility near the longitudinal axis 100 may be minimized in order to limit the effect that elongating the joined topsheet and backsheet has on the absorbent core. For this embodiment, the surface path length of the second regions may vary in that the surface path length near the longitudinal axis is shorter than the surface path length near the longitudinal edges of the chassis 22. The result is a strainable network having minimal extensibility along the longitudinal axis relative to the extensibility along the longitudinal edges of the chassis.

The diaper 20 may include a fastener such as a hook and loop type fastening system 40 including at least one engaging component (male fastening component) and at least one landing zone (female fastening component). The diaper 20 may also include such other features as are known in the art including leg cuffs, waist cap features, elastics and the like to provide better fit, containment and aesthetic characteristics. Such additional features are well known in the art and are described in U.S. Pat. No. 3,860,003; and U.S. Pat. No. 5,151,092, which are incorporated by reference herein.

In addition, the present invention may be suitable for other diaper embodiments including those disclosed in U.S.

Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

Test Methods

Sample preparation:

The samples used for the test described hereunder are 1" wide×4" long with the long axis of the sample cut parallel to the direction of maximum extensibility of the sample. The sample should be cut with a sharp exacto knife or some suitably sharp cutting device designed to cut a precise 1" wide sample. (If there is more than one direction of extensibility of the material, samples should be taken parallel to a representative direction of elongation). The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three samples of a given material are tested.

Hysteresis Test

A hysteresis test is used for measuring the percent set and percent force relaxation of the extensible portion 42 of the joined topsheet 24 and backsheet 26. The tests are performed on an Instron Model 1122, available from Instron Corporation of Canton, Mass. which is interfaced to a Gateway 2000 486/33 Hz computer available from Gateway 2000 of N. Sioux City, S. Dak. 57049, using TestWorks.™. software which is available from Sintech, Inc. of Research Triangle Park, N.C. 27709. All essential parameters needed for testing are input in the TestWorks.™. software for each test (i.e., Crosshead Speed, Maximum percent elongation Point and Hold Times). Also, all data collection, data analysis and graphing are done using the TestWorks.™. software.

The grips of the Instron consist of air actuated grips designed to concentrate the entire gripping force along a single line perpendicular to the direction of testing stress having one flat surface and an opposing surface from which protrudes a half round to minimize slippage of the sample. The sample is mounted in the grips with its long axis perpendicular to the direction of applied percent elongation. The crosshead speed is set to 10 in/min. The crosshead moves to the specified maximum percent elongation and holds the sample at this percent elongation for 30 seconds. After the thirty seconds the crosshead returns to its original position (0% elongation) and remains in this position for 60 seconds. The crosshead then returns to the same maximum percent elongation as was used in the first cycle, holds for thirty seconds and then again returns to zero.

A graph of Grams Force vs. Percent Elongation (X100+100) for the extensible portion 42 of the joined topsheet 24 and backsheet 26 when subjected to 100% elongation and examined for hysteresis response is shown in FIG. 3. According to the present invention, 0 constitutes an unbiased length of the sample, while 0.5 represents a percent elongation which is 150% of the unbiased length; and 2.0 represents a percent elongation which is 200% of the unbiased length. The percent force relaxation is determined by the following calculation of the force data from the first cycle:

$$\% \text{ Force Relaxation} = \frac{\text{Force at Max \% elongation} - \text{Force after 30 Sec. hold}}{\text{Force at Max \% elongation (cycle 1)}} \times 100$$

The percent set is the percent elongation of the sample of the second cycle where the sample starts to resist the elongation. The average percent force relaxation and percent set for three samples is reported for each maximum percent elongation value tested.

Tensile Test

The tensile test is used for measuring extension force (force) versus percent elongation properties and percent available stretch of side panel material. The tests are performed on an Instron Model 1122, available from Instron Corporation of Canton, Mass. which is interfaced to a Gateway 2000 486/33 Hz computer available from Gateway 2000 of N. Sioux City, S. Dak., using TestWorks.™. software which is available from Sintech, Inc. of Research Triangle Park, N.C. All essential parameters needed for testing are input in the TestWorks.™. software for each test. Also, all data collection, data analysis and graphing are done using the TestWorks.™. software.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead elongates the sample until the sample breaks at which point the crosshead stops and returns to its original position (0% elongation).

The percent available stretch is the point at which there is an inflection in the force-elongation curve, beyond which point there is a rapid increase in the amount of force required to elongate the sample further. The average of the percent available stretch for three samples is recorded. A graph of Grams Force vs. Extension (inches) for the side panel material is shown in FIG. 4.

Although particular embodiments of the present invention have been illustrated and described, it would be apparent to those skilled in the art that various other changes and modifications can be made without departing from the spirit of the present invention. It is therefore intended to cover in the appended claims all such changes and modifications that are within the scope of this invention.

What is claimed is:

1. An absorbent article having a longitudinal axis, a transverse axis, and a pair of opposing longitudinal edges, the absorbent article comprising:

a liquid pervious topsheet;

a liquid impervious backsheet joined to the topsheet, wherein the joined topsheet and backsheet includes an extensible portion, the extensible portion being non-elastically, laterally extensible having a percent elongation of at least about 125%, wherein the extensible portion provides size adjustment to permit custom fitting of the absorbent article to a wearer;

an absorbent core disposed between the topsheet and the backsheet; and a pair of elastomeric side panels, each of the side panels is elastically laterally extensible and is joined to a portion of a longitudinal edge near the extensible portion of the joined topsheet and backsheet;

wherein a force required to elongate the side panels a select percent elongation is less than the force required to elongate the extensible portion of the joined topsheet and backsheet an equivalent select percent elongation.

2. The absorbent article of claim 1 wherein the extensible portion of the joined topsheet and backsheet has a percent elongation of at least about 150%.

3. The absorbent article of claim 1 wherein the extensible portion of the joined topsheet and backsheet has a percent elongation of at least about 200%.

4. The absorbent article of claim 1 wherein each of the side panels has a percent elongation of at least about 150%.

5. The Absorbent article of claim 1 wherein the force required to elongate each of the elastomeric side panels laterally about 150% is less than the force required to elongate the extensible portion of the joined topsheet and backsheet laterally about 125%.

6. The Absorbent article of claim 1 wherein the force required to elongate each of the side panels laterally about 200% is less than the force required to elongate the extensible portion of the joined topsheet and backsheet laterally about 150%.

7. The absorbent article of claim 1 wherein the force required to elongate each of the side panels laterally about 125% is less than about 80 g/cm.

8. The absorbent article of claim 1 wherein the force required to elongate each of the side panels laterally about 150% is less than about 180 g/cm.

9. The absorbent article of claim 1 wherein the force required to elongate the extensible portion of the joined topsheet and backsheet laterally about 150% is greater than about 100 g/cm.

10. The absorbent article of claim 1 wherein the force required to elongate the topsheet of the extensible portion laterally about 125% is greater than the force required to extend the backsheet of the extensible portion laterally about 125%.

11. The absorbent article of claim 1 wherein the force required to extend the backsheet of the extensible portion laterally about 125% is greater than the force required to extend the topsheet of the extensible portion laterally about 125%.

12. The absorbent article of claim 1 wherein the extensible portion comprises a third material joined to the topsheet and the backsheet, the third material is laterally extensible wherein the force required to extend the third material laterally about 125% is greater than the force required to extend either the topsheet or the backsheet laterally about 125%.

13. The absorbent article of claim 12 wherein the third material is pleated or folded whereby as the extensible portion is extended laterally, the pleats or folds separate allowing the third material to expand.

14. A disposable diaper having a longitudinal axis, a transverse axis, a longitudinal edge, a first waist region, a second waist region, and a crotch region interposed therebetween, the disposable diaper comprising:

a liquid pervious topsheet;

a liquid impervious backsheet joined to the topsheet, wherein a portion of the second waist region of the joined topsheet and backsheet is non-elastically, laterally extensible at least about 125%, wherein the non-elastically laterally extensible portion of the second waist region provides size adjustment to permit custom fitting of the absorbent article to a wearer;

an absorbent core disposed between the topsheet and the backsheet; and a pair of elastomeric side panels, each of the side panels is elastically laterally extensible and is joined to a portion of a longitudinal edge near the extensible portion of the joined topsheet and backsheet;

wherein a farce required to extend each of the elastomeric side panels a select percent elongation is less than the force required to extend the second waist region an equivalent select percent elongation.

15. The disposable diaper of claim 14 wherein the extensible portion of the second waist region has a percent elongation of at least about 150%.

16. The disposable diaper of claim 14 wherein each of the side panels is elastically laterally extensible having a percent elongation of at least about 150%.

17. The disposable diaper of claim 14 wherein the force required to extend each of the elastomeric side panels about 150% is less than the force required to extend the second waist region laterally about 125%.

18. The disposable diaper of claim 14 wherein the force required to extend each of the side panels laterally about 125% is less than about 80 g/cm.

19. The absorbent article of claim 14 wherein the force required to extend the extensible portion of the second waist region laterally about 150% is greater than about 100 grams/cm.

20. The disposable diaper of claim 14 wherein the extensible portion of the second waist region has a width and each of the side panels has a width, wherein the width of the extensible portion of the second waist region is equal to the width of each of the side panels.

* * * * *

UNITED STATES PATENT AND TRADEMARK OFFICE
CERTIFICATE OF CORRECTION

PATENT NO. : 6,605,070 B2
DATED : August 12, 2003
INVENTOR(S) : Susan J. Ludwig, Gary D. LaVon It is certified that error appears in the above-identified patent and that said Letters Patent is hereby corrected as shown below:

Column 16,
Line 29, delete "farce" and insert therefor -- force --.

Signed and Sealed this

Seventeenth Day of August, 2004

JON W. DUDAS
*Acting Director of the United States Patent and Trademark Office*